(12) United States Patent
Allingham et al.

(10) Patent No.: US 11,311,685 B2
(45) Date of Patent: Apr. 26, 2022

(54) TISSUE LIFTING DEVICES AND METHODS OF USE

(71) Applicants: GEORGIA TECH RESEARCH CORPORATION, Atlanta, GA (US); Duke University, Durham, NC (US)

(72) Inventors: R. Rand Allingham, Durham, NC (US); C. Ross Ethier, Atlanta, GA (US); Jordan David Rehwaldt, Atlanta, GA (US)

(73) Assignees: GEORGIA TECH RESEARCH CORPORATION, Atlanta, GA (US); DUKE UNIVERSITY, Durham, NC (US)

( * ) Notice: Subject to any disclaimer, the term of this patent is extended or adjusted under 35 U.S.C. 154(b) by 28 days.

(21) Appl. No.: 16/468,138

(22) PCT Filed: Dec. 11, 2017

(86) PCT No.: PCT/US2017/065529
§ 371 (c)(1),
(2) Date: Jun. 10, 2019

(87) PCT Pub. No.: WO2018/107144
PCT Pub. Date: Jun. 14, 2018

(65) Prior Publication Data
US 2020/0384212 A1    Dec. 10, 2020

Related U.S. Application Data

(60) Provisional application No. 62/432,196, filed on Dec. 9, 2016.

(51) Int. Cl.
*A61M 5/42*    (2006.01)
*A61F 9/00*    (2006.01)
(Continued)

(52) U.S. Cl.
CPC ........... *A61M 5/425* (2013.01); *A61F 9/0026* (2013.01); *A61M 5/28* (2013.01); *A61M 5/3134* (2013.01);
(Continued)

(58) Field of Classification Search
CPC .......... A61M 5/425; A61M 2210/0612; A61M 5/28; A61M 5/3134; A61M 5/3148;
(Continued)

(56) References Cited

U.S. PATENT DOCUMENTS

| 5,013,295 A | 5/1991 | Dubroff |
| 6,245,043 B1 | 6/2001 | Villette |

(Continued)

FOREIGN PATENT DOCUMENTS

WO    WO-8909070 A1 * 10/1989 .......... A61M 1/0058

OTHER PUBLICATIONS

International Search Report and Written Opinion dated Mar. 6, 2018, from International Application No. PCT/US2017/065529, 9 pages.

*Primary Examiner* — Jason E Flick
(74) *Attorney, Agent, or Firm* — Meunier Carlin & Curfman LLC

(57) ABSTRACT

Various implementations include a tissue lifting device that is operable using one hand. The device includes a housing, an actuator that is slidably moveable through a channel within the housing, and a lifting mechanism adjacent a distal end of the housing. The actuator causes the lifting mechanism to lift a tissue. In some implementations, the housing includes a needle adjacent the distal end of the housing that punctures the tissue and allows for injection of a composition behind the tissue. The lifting mechanism according to (Continued)

some implementations is a suction-based (or aspiration) system. And, in other implementations, the lifting mechanism is a grasping system.

18 Claims, 7 Drawing Sheets

(51) Int. Cl.
*A61M 5/28* (2006.01)
*A61M 5/31* (2006.01)
*A61M 5/315* (2006.01)

(52) U.S. Cl.
CPC ...... *A61M 5/3148* (2013.01); *A61M 5/31513* (2013.01); *A61M 2210/0612* (2013.01)

(58) Field of Classification Search
CPC .............. A61M 5/315; A61M 5/31511; A61M 5/31513; A61M 5/42; A61M 5/422; A61M 5/31; A61M 5/32; A61M 5/178; A61F 9/0026; A61F 9/00; A61F 9/0008
See application file for complete search history.

(56) References Cited

U.S. PATENT DOCUMENTS

| | | | |
|---|---|---|---|
| 6,645,169 B1 | 11/2003 | Slate et al. | |
| 2006/0089607 A1 | 4/2006 | Chen | |
| 2006/0129065 A1 | 6/2006 | Matsumoto | |
| 2008/0312606 A1* | 12/2008 | Harrison | A61M 5/2033 604/218 |
| 2010/0152646 A1 | 6/2010 | Girijavailabhan | |
| 2011/0098647 A1 | 4/2011 | Jennings | |
| 2016/0175528 A1 | 6/2016 | Marshall et al. | |

* cited by examiner

TISSUE LIFTING DEVICES AND METHODS OF USE

CROSS REFERENCE TO RELATED APPLICATIONS

This application claims priority to U.S. Provisional Application No. 62/432,196, entitled "Tissue Lifting Devices and Methods of Use," filed Dec. 9, 2016, the content of which is herein incorporated by reference in its entirety.

BACKGROUND

Glaucoma is an optic neuropathy frequently characterized by elevated intraocular pressure (IOP). It is the second most common cause of blindness, estimated to affect nearly 80 million people by 2020. Glaucoma has no cure, and all clinical treatments seek to lower IOP to slow or halt the progression of vision loss from the disease. Eye drops containing one or more pharmaceutical agents (e.g., beta-blockers, prostaglandin analogs) are the first-line therapy for IOP reduction. However, eye drops as a drug delivery vehicle suffer from multiple drawbacks. Notably, patients must self-administer the drops at least daily, which can be difficult for patients to perform and for healthcare providers to monitor. Studies consistently find significant (>50%) patient non-compliance and/or misadministration of eye drops, which is a major cause of vision loss.

Sustained release formulations for glaucoma medications, which obviates the need for daily dosing, are therefore in development. Such formulations can be delivered intraocularly or subconjunctivally, with the latter being preferred to simplify delivery and lower the risk of complications. Drug delivered to the subconjunctival space acts as a depot for sustained release. Advantages include greater duration of action, more bioavailability (i.e., reduced drug exposure), and improved IOP control. For example, a one-time subconjunctival nanoliposomal latanoprost injection significantly reduced IOP in glaucoma patients at 3 and 6 months post-injection using a fraction of the amount required for a topically applied formulation. Subconjunctival injections have been used by ophthalmologists to deliver a variety of therapeutics to the eye, including steroids, antibiotics, and anesthetics. Subconjunctival injection is a procedure that requires a skilled medical practitioner since, if done incorrectly, there is risk of sight-threatening complications from the needle or the injected agent. For example, there is a risk of puncturing the globe that exposes internal structures, like the retina, with serious visual consequences. Subconjunctival hemorrhage is a common complication of subconjunctival injection, and although not visually debilitating, it is cosmetically objectionable and persistent. Finally, inaccurate drug delivery may cause drug to be injected outside of the eye and be lost, a significant concern since single doses of sustained release medications are expensive.

Current subconjunctival delivery systems include a pair of forceps to grasp and elevate the conjunctiva and a syringe/needle to deliver the medical agent into the subconjunctival space. However, the ease of use, accuracy, and safety of these subconjunctival delivery systems are suboptimal.

Accordingly, there is a need in the art for improved systems and methods for lifting tissue and injecting compositions below the lifted tissue.

BRIEF SUMMARY

Various implementations include a suction-based injection device that comprises a housing, a plunger, and a needle. The housing has a proximal end, a distal end, and a central axis extending between the proximal end and the distal end. The housing defines an aspiration chamber adjacent the proximal end of the housing; an injection chamber adjacent the distal end of the housing; an injectable composition chamber disposed between the aspiration chamber and the injection chamber along the central axis; and at least one connecting channel having a first opening in fluid communication with the injection chamber and a second opening in fluid communication with a proximal portion of the aspiration chamber. The plunger has a proximal end and a distal end. The distal end of the plunger is slidably disposed within the aspiration chamber, and the proximal end of the plunger extends axially from the proximal end of the housing. The needle is disposed within the injection chamber. The needle has a distal end disposed adjacent a distal end of the injection chamber. The proximal portion of the aspiration chamber is defined between a first seal and a second seal. The first seal extends radially between the plunger and the aspiration chamber at a first axial location along the plunger, and the second seal is disposed adjacent the distal end of the aspiration plunger at a second axial location along the plunger. The first axial location is disposed between the second axial location and the proximal end of the housing. The first seal is stationary. The second seal is axially moveable with the plunger. And, an outer diameter of the second seal abuts an inner diameter of the aspiration chamber. A sealed volume is defined by the injection chamber, a surface against which a distal end of the injection chamber is disposed, the connecting channel, and the proximal portion of the aspiration chamber. And, movement of the second seal of the plunger in a distal direction reduces a pressure in the injection chamber.

In some implementations, the plunger is an aspiration plunger, and the device further comprises an injection plunger. The injection plunger includes a proximal end and a distal end. The proximal end of the injection plunger is disposed distally of the second seal of the aspiration plunger along the central axis.

In some implementations, a third seal is disposed adjacent the distal end of the injection plunger. The third seal has an outer diameter that abuts an inner diameter of the injection chamber.

In some implementations, a compression spring is disposed between the proximal end of the injection plunger and the distal end of the aspiration plunger, and a minimal force required to compress the compression spring is greater than a force required to move the injection plunger distally through the injectable composition chamber. In further implementations, the housing further defines at least one aspiration reset channel that has a first opening defined by a radial wall of the aspiration chamber and a second opening defined by an exterior surface of the housing. The first opening is in communication with the sealed volume upon the distal end of the aspiration plunger compressing the spring.

In some implementations, an injectable composition is disposed within the injectable composition chamber. In certain implementations, the injectable composition comprises a therapeutic or diagnostic agent.

In some implementations, the injectable composition is disposed within a cartridge, and the cartridge is disposed within the injectable composition chamber.

In some implementations, the distal end of the injection chamber has an elliptical cross sectional shape as taken through a plane that is orthogonal to the central axis.

In some implementations, the distal end of the injection chamber has a circular cross sectional shape as taken through a plane that is orthogonal to the central axis.

In some implementations, the distal end of the injection chamber has an arcuate cross sectional shape as taken through a plane that includes the central axis.

In some implementations, the distal end of the injection chamber is coated with at least one bioadhesive agent. For example, in certain implementations, the bioadhesive agent is a mucoadhesive polymer.

In some implementations, an exterior surface of the housing adjacent the proximal end of the housing defines at least one flange that extends radially outwardly from the proximal end.

In some implementations, the needle is stationary within the device.

In some implementations, the at least one connecting channel comprises a first connecting chamber and a second connecting channel.

Various other implementations include a method of delivering an injectable composition using a one-handed operable injection device. The device comprises a housing having a proximal end and a distal end. The method includes: (1) disposing the distal end of the one-handed operable injection device against a bodily tissue; (2) applying a suction force to the distal end of the one-handed operable injection device to lift the bodily tissue toward the distal end of the one-handed injection device; (3) injecting an injectable composition into the lifted bodily tissue; and (4) releasing the suction force.

In some implementations, applying the suction force comprises applying a vacuum source that is separate from the one-handed operable device. The vacuum source is in fluid communication with the distal end of the device.

In some implementations, applying the suction force comprises pushing a plunger of the one-handed operable device along a central axis of the device toward the distal end of the device. A portion of the plunger disposed within the device is disposed within a closed volume of air, and the closed volume of air includes the distal end of the device.

In some implementations, the housing defines an aspiration chamber adjacent the proximal end of the housing, at least one connecting channel having a first opening and a second opening, and an injection chamber adjacent the distal end of the housing. A first seal extends radially between the plunger and the aspiration chamber, and a second seal is disposed adjacent a distal end of the plunger. The first and second seals are axially spaced apart. The first seal is stationary, and the second seal is axially movable with the plunger. The second seal is disposed distally of the first seal along the central axis, and the second seal has an outer diameter that abuts an inner diameter of the aspiration chamber. The first opening of the connecting channel is defined by the injection chamber. The second opening of the connecting channel is defined by the aspiration chamber and is disposed between the first seal and the second seal. The closed volume is defined by the injection chamber, the bodily tissue adjacent a distal end of the injection chamber, the connecting channel, and the volume between the first and second seals within the aspiration chamber. And, applying the suction force comprises axially moving a distal end of the plunger and the second seal through at least a portion of the aspiration chamber such that the volume between the first and second seals increases with the axial movement of the plunger.

In some implementations, the one-handed operable device further comprises a needle, and at least a distal end of the needle is disposed adjacent the distal end of the housing. Applying the suction force further comprises lifting the tissue into contact with the needle such that the needle penetrates the lifted tissue.

In some implementations, the plunger is an aspiration plunger, and the one-handed operable device further comprises an injection plunger. The injection plunger includes a proximal end and a distal end, wherein the proximal end of the injection plunger is disposed distally of the second seal of the aspiration plunger along the central axis. The housing further defines an injectable composition chamber comprising an injectable composition. The injectable composition chamber is disposed between the injection chamber and the aspiration chamber, and injecting the injectable composition comprises urging the distal end of the injection plunger axially through the injectable composition chamber such that the injectable composition is urged out of the injectable composition chamber and into the needle penetrating the lifted bodily tissue.

In some implementations, urging the distal end of the injection plunger through the injectable composition chamber causes the distal end of the aspiration plunger to move distally.

In some implementations, the injection plunger and the aspiration plunger are axially aligned, and a compression spring is disposed between the proximal end of the injection plunger and the distal end of the aspiration plunger. A force required to compress the spring is greater than a force required to move the injection plunger axially through the device.

In some implementations, the housing defines at least one aspiration reset channel. The aspiration reset channel comprises a first opening defined by the aspiration chamber and a second opening defined by an external surface of the housing. Releasing the suction force comprises urging the distal end of the aspiration plunger against the compression spring such that the second seal passes distally of the first opening of the aspiration reset channel to allow air into the closed volume.

In some implementations, the bodily tissue is a conjunctiva, and injecting the injectable composition comprises subconjunctivally dispensing the injectable composition via a needle.

In some implementations, the needle is stationary relative to the distal end of the housing.

In some implementations, the method further includes axially moving the needle prior to dispensing the injectable composition.

Various other implementations include a tissue lifting device that comprises a housing, an actuator, and at least two grasping arms. The housing has a proximal end, a distal end, and a central longitudinal axis extending there between. The housing defines a channel along at least a portion of the central longitudinal axis adjacent the proximal end. The actuator has a proximal end and a distal end. At least a portion of the distal end of the actuator is slidably movable through the channel along the central longitudinal axis of the housing. Each of the two grasping arms has a free end disposed adjacent the distal end of the housing and a fixed end coupled to the housing proximally from the distal end. The arms are bendable about the fixed end. The sliding movement of the actuator urges the free ends of the grasping arms toward each other.

In some implementations, the actuator comprises a central arm and at least one peripheral surface. The central arm is disposed within the housing, and the at least one peripheral surface is radially spaced apart from the central arm and an exterior surface of the housing. The slidable movement of the actuator urges a distal end of the peripheral surface of the actuator into contact with the two grasping arms between the fixed ends and the free ends, causing the free ends of the grasping arms to move laterally toward each other.

In some implementations, the device further includes an injectable composition housing defining an injectable composition chamber. At least a portion of the injectable composition housing is disposed within the channel defined by the housing adjacent the distal end of the housing, and the device further comprises a needle disposed distally of the injectable composition housing. The needle is in fluid communication with the injectable composition chamber. The slidable movement of the actuator toward the distal end of the housing causes an injectable composition stored within the injectable composition chamber to move through the needle.

In some implementations, the injectable composition housing is slidably disposed within the channel, and the needle is slidably moveable relative to the housing.

In some implementations, the device further includes an injection plunger disposed along the central longitudinal axis of the housing and distally of the actuator. The injection plunger has a proximal end disposed axially adjacent the distal end of the central arm of the actuator and a distal end disposed in communication with the injectable composition chamber. Slidable movement of the distal end of the central arm of the actuator toward the distal end of the housing urges the distal end of the central arm into contact with the proximal end of the injection plunger, causing axial movement of the distal end of the injection plunger through the injectable composition chamber to urge the injectable composition through the needle.

In some implementations, the device further includes a spring disposed adjacent the proximal end of the injection plunger and the distal end of the central arm. The spring is compressible by the distal end of the central arm to allow the distal end of the central arm to engage the proximal end of the injection plunger.

In some implementations, the spring is first spring, and the device comprises a second spring. The second spring is disposed adjacent a distal end of the injectable composition housing and the free ends of the grasping arms. The first spring is stiffer than the second spring.

Various other implementations include a tissue lifting device that comprises a housing, a plunger, and an injection chamber defined by a distal end of the housing. The housing has a proximal end and a central longitudinal axis extending between the proximal and distal ends. The housing defines a channel along at least a portion of the central longitudinal axis adjacent the proximal end. The plunger has a proximal end and a distal end. The distal end of the plunger is slidably movable through the channel along the central longitudinal axis of the housing. And, the injection chamber defines a sealed volume with a surface of a tissue against which the distal end of the housing is disposable. The distal end of the plunger is slidable toward the distal end of the housing to reduce a pressure within the injection chamber and cause tissue adjacent the injection chamber to lift into the injection chamber.

In some implementations, the housing is an inner housing, and the device further comprises an outer housing disposed radially outwardly and adjacent the inner housing. The outer housing defines an axial channel, and the inner housing is axially slidable within the axial channel of the outer housing. The distal ends of the inner housing and outer housing define the injection chamber, and axial movement of the distal end of the plunger toward the distal end of the inner housing urges the distal end of the inner housing proximally, reducing the pressure in the injection chamber.

In some implementations, the device includes at least one resilient tab. The resilient tab has a distal end coupled to the outer housing, a proximal end coupled to the inner housing, and an intermediate portion disposed between the proximal end and the distal end of the tab. The intermediate portion extends into the channel of the inner housing. Urging the plunger against the intermediate portion urges the intermediate portion radially outwardly, causing the proximal end of the tab and the inner housing to move axially proximally relative to the outer housing.

In some implementations, the device includes an injectable composition housing. At least a portion of the injectable composition housing is disposed within the inner housing adjacent the distal end of the inner housing. The injectable composition housing defines an injectable composition chamber, and the device further comprises a needle disposed distally of the injectable composition housing. The needle is in fluid communication with the injectable composition chamber. Slidable movement of the plunger toward the distal end of the inner housing causes an injectable composition stored within the injectable composition chamber to move through the needle.

In some implementations, the injectable composition housing is slidably moveable within the inner housing, and slidable movement of the injectable composition housing slidably moves the needle is axially relative to the housing.

In some implementations, the plunger is a first plunger, the device further comprising a second plunger disposed along the central longitudinal axis of the inner housing and distally of the first plunger. The second plunger has a proximal end disposed axially adjacent the distal end of the first plunger and a distal end disposed within the injectable composition chamber. Slidable movement of the distal end of the first plunger toward the distal end of the inner housing urges the distal end of the first plunger into contact with the proximal end of the second plunger, causing axial movement of the distal end of the second plunger through the injectable composition chamber to urge the injectable composition through the needle.

In some implementations, the device further includes a spring disposed distally of the distal end of the first plunger. The spring has a portion that extends axially between the proximal end of the second plunger and the distal end of the first plunger. The spring is compressible by the distal end of the first plunger.

In some implementations, the spring is first spring, and the device comprises a second spring. The second spring is disposed between a distal end of the injectable composition housing and a distal end of the inner housing. The first spring is stiffer than the second spring, and compression of the second spring allows axial movement of the injectable composition housing relative to the inner housing.

BRIEF DESCRIPTION OF THE DRAWINGS

Various implementations are explained in even greater detail in the following example drawings. The drawings are merely examples to illustrate the structure of various devices and certain features that may be used singularly or in combination with other features. The invention should not be limited to the implementations shown.

DETAILED DESCRIPTION

Figure 1A:
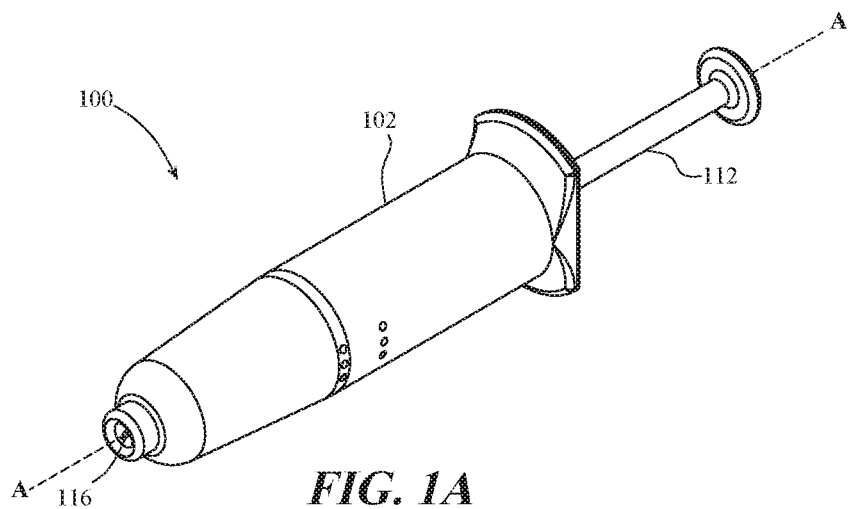
FIGS. 1A-1G illustrate an injection device according to one implementation.
Figure 1B:
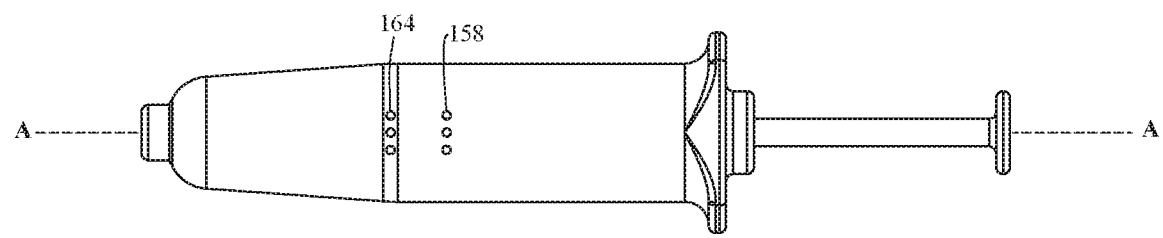

Various implementations include a tissue lifting device that is operable using one hand. The device includes a housing, an actuator that is slidably moveable through a channel within the housing, and a lifting mechanism adjacent a distal end of the housing. The actuator causes the lifting mechanism to lift a tissue. In some implementations, the housing includes a needle adjacent the distal end of the housing that punctures the tissue and allows for injection of a composition behind the tissue. The lifting mechanism according to some implementations is a suction-based (or aspiration) system. And, in other implementations, the lifting mechanism is a grasping system.

For example, various implementations are useful for lifting the conjunctiva, safely separating it from the vascularized, underlying tissue. The needle penetrates the conjunctiva through controlled needle action, preventing globe puncture, and delivers an injectable composition (e.g., a controlled fluid volume or injectable composition) to the subconjunctival space. The one-handed operation of the device provides easier, safer and more reliable injections than the existing forceps-and-syringe approach. Various implementations improve the ease, safety, and outcomes of subconjunctival injections.

FIGS. 1A-1G illustrate a suction-based tissue lifting device 100 according to one implementation. The device 100 includes a housing 102, an aspiration plunger 112, an injection plunger 114, and a needle 116. The housing 102 defines an aspiration chamber 104, an injectable composition chamber 106, an injection chamber 108, a first connecting channel 110a, and a second connecting channel 110b.

The housing 102 includes a proximal end 118 and a distal end 120, and a central axis A-A extends between the proximal end 118 and the distal end 120. The aspiration chamber 104 is adjacent the proximal end 118 of the housing 102. For example, in the implementation shown in FIG. 1A-1G, the aspiration chamber 104 extends between an opening 168 defined in the proximal end 118 of the housing 102 through which the aspiration plunger 112 extends and a distal end 152 of the aspiration chamber 104. The aspiration chamber 104 includes a first portion 172 having a first diameter and a second portion 174 having a second diameter, wherein the first diameter is less than the second diameter. The first portion 172 extends from the proximal end 118 of the housing 102 to a proximal end 154 of the second portion 174, and the second portion 174 extends from its proximal end 154 to its distal end 152.

The injection chamber 108 is adjacent the distal end 120 of the housing 102. The injectable composition chamber 106 is disposed between the aspiration chamber 104 and the injection chamber 108 along the central axis A-A. The connecting channels 110a, 110b each have a first opening 122 that is in fluid communication with the injection chamber 108 and a second opening 124 that is in fluid communication with a proximal portion 126 of the aspiration chamber 104. The second opening 124 is adjacent and distal of the proximal end 154 of the second portion 174 of the aspiration chamber 104. Although two connecting channels are shown in this implementation, other implementations include one or more connecting channels.

The aspiration plunger 112 has a proximal end 128 and a distal end 130. The distal end 130 of the aspiration plunger 112 is slidably disposed within the aspiration chamber 104, and the proximal end 128 of the aspiration plunger 112 is disposed outside of the housing 102 and axially adjacent the proximal end 118 of the housing 102. A first seal 140 extends radially between the aspiration plunger 112 and the aspiration chamber 104 at a first axial location along the aspiration plunger 112. A second seal 142 is disposed adjacent the distal end 130 of the aspiration plunger 112 at a second axial location. The first axial location is between the proximal end 118 of the housing 102 and the second axial location. For example, the second seal 142 shown in FIGS. 1C-1G is a cap that is coupled to the distal end 130 of the aspiration plunger 112. The cap 142 has an outer diameter that corresponds to an inner diameter of the second portion 174 of the aspiration chamber 104 and seals the aspiration chamber 104 between the first seal 140 and the cap 142. The first seal 140 is stationary. Thus, the first seal 140 does not move as the aspiration plunger 112 is slidably moved within the aspiration chamber 104. However, the second seal 142 is coupled to the aspiration plunger 112 and moves axially with the aspiration plunger 112. The proximal portion 126 of the aspiration chamber 104 is the portion of the aspiration chamber 104 that is between the first seal 140 and the second seal 142.

In other implementations, the second seal 142 is annular shaped and extends radially between the aspiration plunger 112 and the aspiration chamber 104 at a second axial location along the aspiration plunger 112. The second axial location is at or adjacent the distal end 130 of the aspiration plunger 112. In some implementations, the second seal 142 is formed with the aspiration plunger 112, and in other implementations, the second seal 142 is separately formed and coupled to the aspiration plunger 112. For example, the second seal 142 may be coupled prior to axial movement of the aspiration plunger 142 or coupled in response to the axial movement of the aspiration plunger 112.

At least a portion of the needle 116 is disposed within the injection chamber 108. The needle 116 includes a proximal end 134 coupled to the injectable composition chamber 106 and in fluid communication therewith and a distal end 136 disposed adjacent a distal end 138 of the injection chamber 108. In some implementations, the distal end 136 of the needle 116 is flush with a portion of the surface of the distal end 138 of the injection chamber 108. However, in other implementations, the distal end 136 of the needle 116 is disposed proximally of the distal end 138 of the injection chamber 108.

Figure 1C:
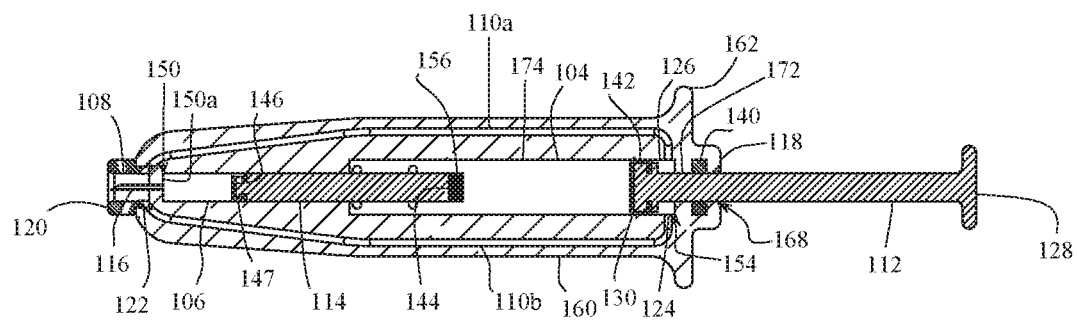
Figure 1D:
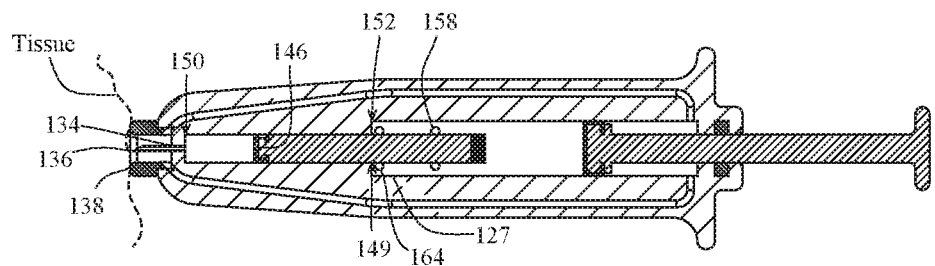
Figure 1E:
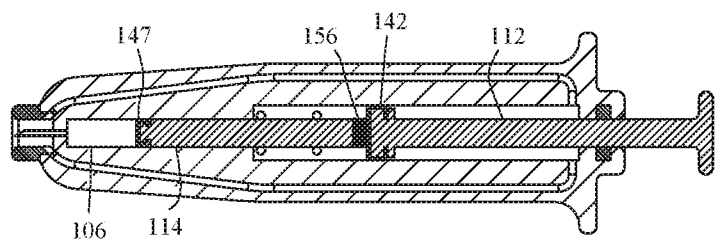

The injection plunger 114 includes a proximal end 144 and a distal end 146. The proximal end 144 of the injection plunger 114 is disposed distally of the second seal 142 of the aspiration plunger 112 along the central axis A-A. In a pre-delivery position of the injection plunger 114, which is shown in FIGS. 1C-1E, the proximal end 144 of the injection plunger 114 is disposed within the aspiration chamber 104, and the distal end 146 of the injection plunger 114 is disposed within the injectable composition chamber 106. For example, in the implementation shown in FIG. 1D, the distal end 146 of the injection plunger 114 is disposed between a proximal end 149 of the injectable composition chamber 106 and a distal end 150 of the injectable composition chamber 106. However, in other implementations, the distal end 146 of the injection plunger 114 may be disposed adjacent the proximal end 149 of the injectable composition chamber 106.

A seal 147 is disposed adjacent the distal end 146 of the injection plunger 114. The seal 147 is a cap that has an outer diameter that abuts the inner diameter of the injectable composition chamber 106. The cap 147 is coupled to the distal end 146 of the injection plunger 114. As the injection plunger 114 is moved axially through the injectable composition chamber 106, the seal 147 urges an injectable composition stored within the injectable composition chamber 106 into the needle 116. In other implementations, the seal is annularly shaped and is coupled around the injection plunger 114 such that the seal extends radially between the injection plunger 114 and the injectable composition chamber 106. In some implementations, the cap 147 is formed with the injection plunger 114, and in other implementations, the cap 147 is separately formed and coupled to the injection plunger 114. For example, the cap 147 may be coupled prior to axial movement of the injection plunger 114 or coupled in response to the axial movement of the injection plunger 114.

In some implementations, the injectable composition is a therapeutic or diagnostic agent.

The contour of the distal end 138 of the injection chamber 108 is circular as viewed from the end of the device 100 (see FIG. 1A) and straight as viewed from a side of the device (see FIGS. 1B-1G). Furthermore, the surface of the distal end 138 of the injection chamber 108 includes a toroidal (or arcuate) shape to allow for better adhesion to the tissue and to prevent puncturing or injuring the tissue to be lifted. In some implementations, the straight contour may be perpendicular to the axis A-A, such as is shown in FIGS. 1A-1G, and in other implementations, the straight contour may be disposed at an angle between 0° and 90° from the central axis A-A.

Figure 3A:
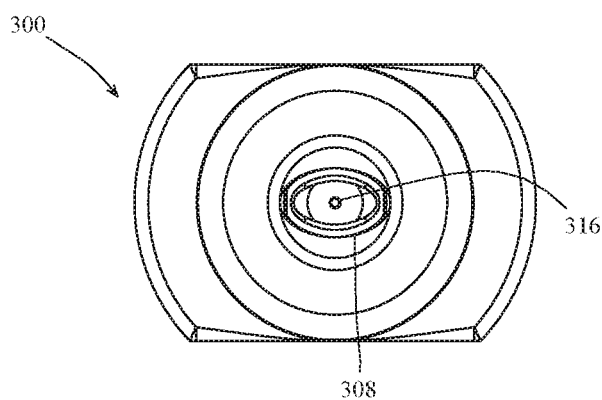
FIGS. 3A-3C illustrate an injection device according to another implementation.
Figure 3B:
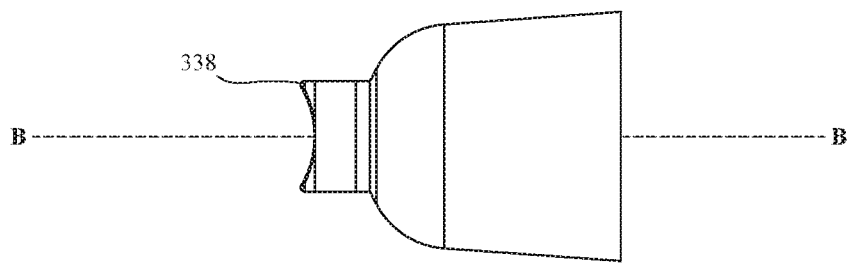
Figure 3C:
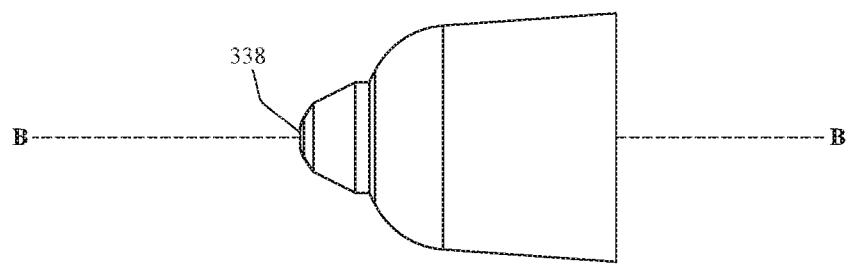

In other implementations, the contour of the distal end 138 of the injection chamber 108 is selected based on the shape of the surface of the tissue to be lifted. For example, if the surface is spherical with a known diameter, such as the eye globe, the contour of the distal end may be selected to fit against a portion of the spherical surface. The implementation in FIGS. 3A-3C illustrates one implementation of device 300 that is useful with a spherical surface. The distal end 338 of the injection chamber 308 of the device 300 is arcuate as viewed from a plane that includes the central axis B-B, as shown in FIGS. 3B and 3C, and elliptical as viewed from a plane that is perpendicular to the central axis B-B, as shown in FIG. 3A. In particular, the contour of the distal end 338 from a first side view of the device is concave (FIG. 3B), and the contour of the distal end 338 from a second side view of the device that is 901° from the first side view is convex (FIG. 3C).

The distal end 138 of the injection chamber 108 can be coated with at least one bioadhesive agent, which includes any substance that promotes coupling, or adhesion, of the distal end 138 to the tissue surface. Examples of bioadhesive agents include mucoadhesive compositions, such as mucoadhesive polymers. Examples of mucoadhesive polymers include biodegradable mucoadhesive polymers (e.g., chitosan, polyethylene oxide, polyphosphazenes, polyanhydrides, polyphosphoesters, polyorthoesters, poly (lactides), poly(glycolides), poly(lactide-coglycolides), polycaprolactones, and polyalkyl cyanoacrylates), biocompatible mucoadhesive polymers (e.g., esters of hyaluronic acid, polyvinyl acetate, and ethylene glycol), synthetic mucoadhesive polymers (e.g., polyvinyl alcohol, polyamides, polycarbonates, polyalkylene glycols, polyvinyl ethers, esters, halides, polymethacrylic acid, polymethyl methacrylic acid, methylcellulose, ethyl cellulose, hydroxypropyl cellulose, hydroxypropyl methylcellulose, and sodium carboxymethylcellulose), and natural mucoadhesive polymers (e.g., sodium alginate, pectin, tragacanth, gelatin, and carrageenan).

In operation, the distal end 138 of the injection chamber 108 is disposed against a tissue, and a sealed volume is defined by the injection chamber 108, the tissue, the connecting channels 110a, 110b, and the proximal portion 126 of the aspiration chamber 104. The aspiration plunger 112 is moved axially through the aspiration chamber 104 from a pre-aspiration position shown in FIGS. 1A-1C to a post-aspiration position shown in FIG. 1F. As the aspiration plunger 112 is moved from the pre-aspiration position to the post-aspiration position, air pressure in the injection chamber 108 is reduced, which pulls the tissue into the injection chamber 108. In the pre-aspiration position, the second seal 142 is disposed adjacent the proximal end 154 of the second portion 174 of the aspiration chamber 104. FIG. 1D illustrates the aspiration plunger 112 as the second seal 142 and distal end 130 of the aspiration plunger 112 are moved axially through the aspiration chamber 104 toward the distal end 152 of the aspiration chamber 104.

Figure 1F:
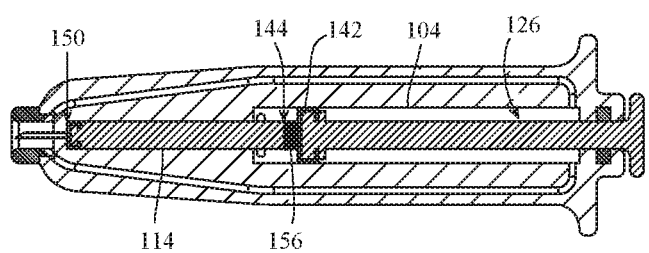

The needle 116 penetrates the lifted tissue as the tissue is lifted into the injection chamber 108. Thus, in this implementation, the needle 116 is stationary. After the tissue is penetrated by the needle 116, the aspiration plunger 112 is moved further distally to urge the injection plunger 114 distally so as to urge the injectable composition in the injectable composition chamber 106 through the needle 116 and under the lifted tissue. FIG. 1E illustrates the injection plunger 114 and the aspiration plunger 112 in their pre-delivery positions, and FIG. 1F illustrates the injection plunger 114 and the aspiration plunger 112 in their post-delivery positions. In the post-delivery position of the injection plunger 114, the distal end 146 of the injection plunger 114 is disposed adjacent the distal end 150 of the injectable composition chamber 106.

The device 100 further includes a spring 156 that is disposed along the central axis A-A between the proximal end 144 of the injection plunger 114 and the distal end 130 of the aspiration plunger 112. For example, as shown in FIGS. 1C and 1D, the spring 156 is coupled to the proximal end 144 of the injection plunger 114. The distal end 130 of the aspiration plunger 112 is axially urged into contact with the spring 156, as shown in a pre-delivery position of the injection plunger 114 in FIG. 1E, and continued axial movement of the aspiration plunger 112 in the distal direction moves the distal end 146 of the injection plunger 114 toward the distal end 150 of the injectable composition chamber 106. As the injection plunger 114 moves through the injectable composition chamber 106, the seal 147 of the injection plunger 114 moves the injectable composition through the needle 116.

The stiffness of the spring 156 is selected so that during movement of the injection plunger 114 from the pre-delivery position to the post-delivery position, the spring 156 does not compress or compresses minimally. Thus, the force required to compress the spring 156 is greater than the force required to urge the injection plunger 114 to the post-delivery position.

Throughout operation, a distal portion 127 of the aspiration chamber 104 remains at atmospheric pressure through one or more atmospheric channels 164 that extend radially from a first opening defined by the aspiration chamber 104 to a second opening defined by an exterior surface 160 of the housing 102. The distal portion 127 of the aspiration chamber 104 is defined between the second seal 142 and the distal end 152 of the aspiration chamber 104. The first opening of each atmospheric channels 164 is defined adjacent the distal end 152 of the aspiration chamber 104. In the implementation shown in FIGS. 1A-1G, the device 100 includes a row of three atmospheric channels 164.

The device 100 also includes one or more aspiration reset channels 158 that extend radially from a first opening defined by the aspiration chamber 104 to a second opening defined by an exterior surface 160 of the housing 102. The first opening of each aspiration reset channel 158 is disposed within the distal portion 127 of the aspiration chamber and proximally of a plane that includes the most proximal atmospheric channel 164 and is perpendicular to the central axis A-A. When the aspiration plunger 112 is in the post-delivery position, as shown in FIG. 1F, the second seal 142 of the aspiration plunger 112 is radially aligned with the first openings of the aspiration reset channels 158, which blocks air from entering the proximal portion 126 of the aspiration chamber 104 through the channels 158 and maintains suction of the lifted tissue. In another implementation, the second seal 142 is disposed proximally of the first openings of the aspiration reset channels 158 in the aspiration plunger's 112 post-delivery position, which prevents air flowing through channels 158 from entering the proximal portion 126 of the aspiration chamber 104.

Figure 1G:
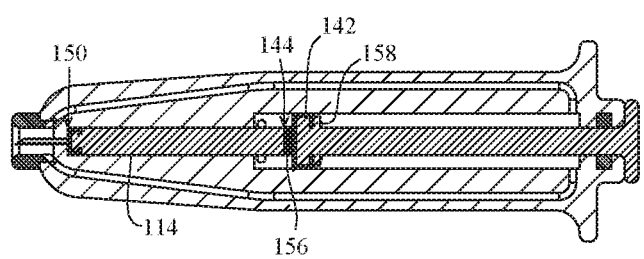

After the injectable composition is delivered from the injectable composition chamber 106 through the needle 116, the distal end 146 of the injection plunger 114 is positioned at shoulder 150a defined by the distal end 150 of the injectable composition chamber 106. Further movement of the aspiration plunger 112 in the distal direction to an aspiration reset position, which is shown in FIG. 1G, causes the distal end 130 of the aspiration plunger 112 to compress the spring 156 against the proximal end 144 of the injection plunger 114. The distance that the spring 156 travels between the uncompressed and compressed configurations is selected such that the spring 156 moves a sufficient distance to allow the second seal 142 to move axially past the first openings of the aspiration reset channels 158, which allows air to enter the sealed volume of the proximal portion 126 of the aspiration chamber 104 and release the suction force on the tissue. Upon removal of the axial force on the aspiration plunger 112 in the distal direction, the spring 156 urges the distal end 130 of the aspiration plunger 112 proximally back to the aspiration plunger's post-delivery position shown in FIG. 1E.

A flange 162 disposed adjacent the proximal end 118 of the housing 102 extends radially outwardly from at least a portion of the external surface 160 of the housing 102. In some implementations, the flange 162 includes two or more portions that are circumferentially spaced apart around the external surface 160. And, in other implementations, the flange 162 extends less than 360° around the external surface 160. In yet another implementation, the flange 162 extends around the full perimeter of the external surface 160 of the housing 102 but has a non-circular cross sectional shape as viewed in a plane that extends perpendicular to the axis A-A. For example, the cross sectional shape may be elliptical, rectangular, or other polygonal shape that prevents the housing 102 from rolling when placed on a surface.

Figure 2A:
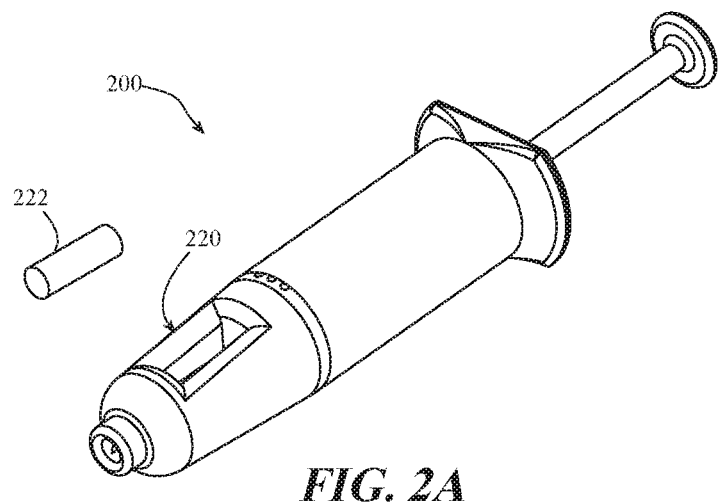
FIGS. 2A-2C illustrate an injection device according to another implementation.
Figure 2B:
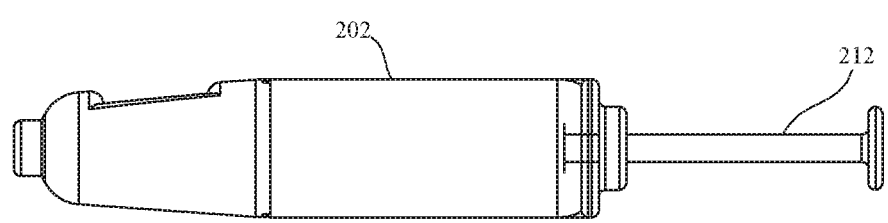
Figure 2C:
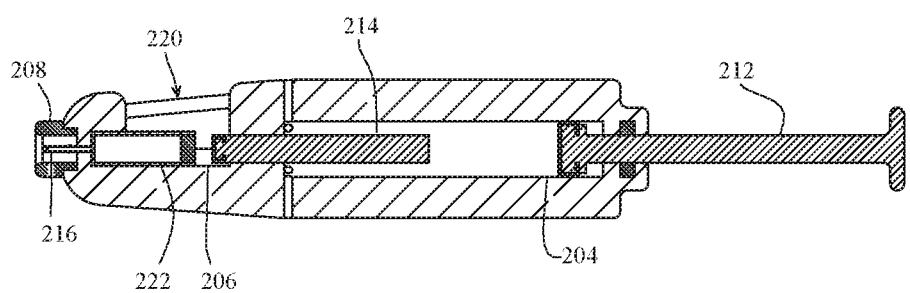

FIGS. 2A-2C illustrate a suction-based tissue lifting device 200 according to another implementation. The device 200 is similar to device 100. However, the spring 156 and aspiration reset channels 158 are not included in the device 200. Additionally, the injectable composition is disposed within a cartridge 222. The cartridge 222 is inserted into the injectable composition chamber 206 through opening 220 defined by the housing 202. The aspiration plunger 212 is urged through the aspiration chamber 204, as described above in relation to FIGS. 1A-1G, and the aspiration plunger 212 urges the injection plunger 214 through the injectable composition chamber 206 to dispense the injectable composition within the cartridge 222 into needle 216 disposed within the injection chamber 208.

Figure 4A:
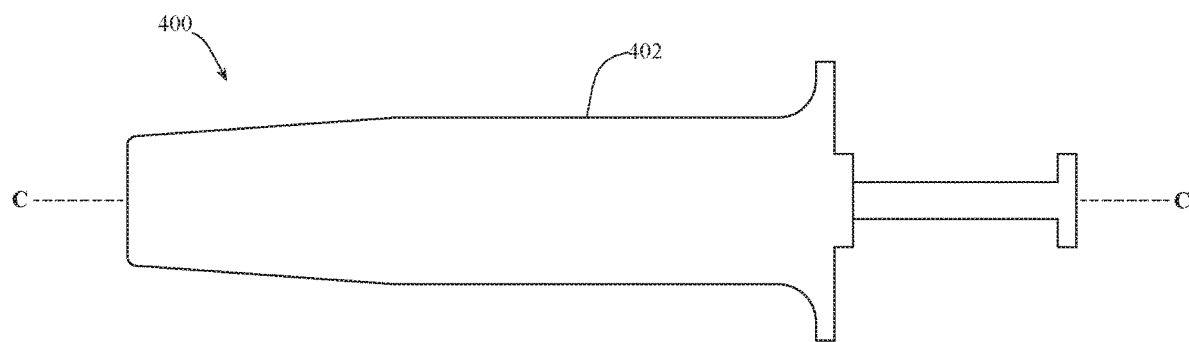
FIGS. 4A and 4B illustrate an injection device according to another implementation.
Figure 4B:
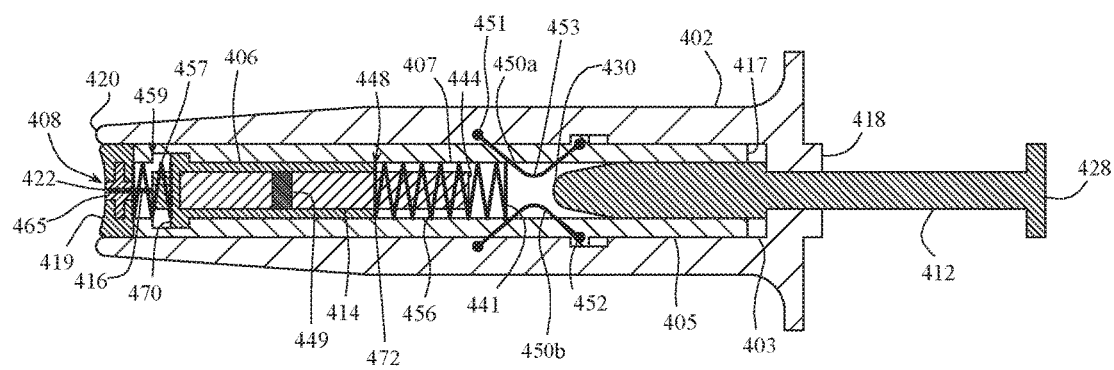

FIGS. 4A and 4B illustrate a suction-based tissue lifting device 400 according to another implementation. The device 400 includes an outer housing 402, an inner housing 405, an aspiration plunger 412, an injection plunger 414, resilient tabs 450a, 450b, a first spring 457, a second spring 456, an injectable composition housing 406, and a needle 416 coupled to the injectable composition housing 406.

The outer housing 402 has a proximal end 418, a distal end 420, and a central longitudinal axis C-C extending there between. An axial channel 403 is defined along at least a portion of the central longitudinal axis C-C adjacent the proximal end 418.

The inner housing 405 is disposed radially within the axial channel 403 of the outer housing 402. The inner housing 405 includes a proximal end 417 and a distal end 419, and a central axis of the inner housing 405 is coaxial with the central axis C-C of the outer housing 402. The inner housing 405 defines a channel 407. The inner housing 405 is axially slidable within the axial channel 403 of the outer housing 402.

The distal ends 420, 419 of the outer 402 and inner housings 405, respectively, define an injection chamber 408. The injection chamber 408 and a surface of a tissue against which the distal end 420 of the outer housing 402 is disposed define a sealed volume.

The aspiration plunger 412 has a proximal end 428 and a distal end 430, and the distal end 430 of the aspiration plunger 412 is slidably movable through the channel 407 of the inner housing 405 along the central longitudinal axis C-C.

Resilient tabs 450a, 450b each have a distal end 451 coupled to the outer housing 402, a proximal end 452 coupled to the inner housing 405, and an intermediate portion 453 disposed between the proximal end 452 and the distal end 451 of the each tab 450a, 450b. The intermediate portion 453 extends into the channel 407 of the inner housing 405. Radially outward pressure on the intermediate portion 453 causes each tab 450a, 450b to flatten, increasing the distance between the proximal end 452 and the distal end 451 of each tab 450a, 450b.

The aspiration plunger 412 has an outer diameter that is greater than the radial distance between the intermediate portions 453 when the distal end 430 of the aspiration plunger 412 is disposed proximally of the intermediate portions 453. Thus, when the distal end 430 of the aspiration plunger 412 is urged toward the distal end 419 of the inner housing 405 and the aspiration plunger 412 moves between the intermediate portions 453, the aspiration plunger 412 provides radially outward pressure on the intermediate portions 453 of the tabs 450a, 450b, causing the proximal ends 452 of the tab 450a, 450b to move axially proximally relative to the outer housing 402 and the inner housing 405 to move proximally within the channel 403 of the outer housing 402.

Because the volume of between the distal ends 419, 420 and the tissue is sealed, the proximal movement of the distal end 419 of the inner housing 405 relative to the distal end 420 of the outer housing 402 increases the volume of the injection chamber 408 defined by the tissue adjacent the distal end 420 of the outer housing 402 and the distal end 419 of the inner housing 405, which reduces the pressure in the injection chamber 408 and causes the tissue to be lifted into the injection chamber 408.

The injectable composition housing 406 is slidably disposed within the channel 407 of the inner housing 405 adjacent the distal end 419 of the inner housing 405. The needle 416 is coupled to a distal end 470 of the injectable composition housing 406 and is in fluid communication there with. The distal end 422 of the needle 416 extends through a seal 465 disposed adjacent the distal end 419 of the inner housing 405 in response to the injectable composition housing 406 being moved distally through channel 407. The seal 465 prevents fluid from moving into the injection chamber 408 but allows the distal end 422 of the needle 416 to extend through the seal 465 and penetrate the tissue within the injection chamber 408.

The injection plunger 414 is disposed distally of the aspiration plunger 412. The injection plunger 414 includes a proximal end 444 and a distal end 449. The proximal end 444 is disposed axially adjacent the distal end 430 of the aspiration plunger 412, and the distal end 449 is disposed adjacent a proximal end 448 of the injectable composition housing 406.

The first spring 457 is disposed between a distal end 470 of the injectable composition housing 406 and the distal end 419 of the inner housing 405. At least a portion of the second spring 456 is disposed between the proximal end 448 of the injectable composition housing 406 and the distal end 430 of the aspiration plunger 412. The second spring 456 extends around at least a proximal portion of the injection plunger 414, and a proximal end 441 of the second spring 456 in an uncompressed state extends proximally of the proximal end 444 of the injection plunger 414. A distal end 472 of the second spring 456 is distal of the proximal end 444 of the injection plunger 414. The second spring 456 is stiffer than the first spring 457.

In operation, as the distal end 430 of the aspiration plunger 412 is urged distally through the channel 407 of the inner housing 405, the distal end 430 of the aspiration plunger 412 engages the distal end 472 of the second spring 456, which translates the axial movement of the aspiration plunger 412 to axially move the injectable composition housing 406 distally, with no or minimal compression of the second spring 456. Once the force on the aspiration plunger 412 overcomes the stiffness of the first spring 457, the first spring 457 compresses and allows the distal end 422 of the needle 416 to move through the seal 465 and penetrate the tissue lifted into the injection chamber 408. Thus, in this implementation, the needle 416 is moved axially to penetrate the tissue lifted into the injection chamber 408.

Upon moving the distal end 422 of the needle 416 through the seal 465, the distal end 470 of the injectable composition chamber 406 abuts a shoulder 459 defined by the distal end 419 of the inner housing 405, and additional force on the aspiration plunger 412 compresses the second spring 456, which allows the distal end 430 of the aspiration plunger 412 to engage the proximal end 444 of the injection plunger 414 and urge the injection plunger 414 distally through the injectable composition housing 406 to push the injectable composition through the needle 416.

Because the aspiration occurs prior to the distal end 430 of the aspiration plunger 412 engaging the second spring 456, and because more force is required to compress the second spring 456 than the first spring 457, the device 400 is operable with one hand to sequentially lift the tissue, penetrate the needle into the tissue, and deliver the injectable composition. Furthermore, when the procedure is finished, the release of the second spring 456 urges the aspiration plunger 412 in a proximal direction and out of contact with the intermediate portions 453 of tabs 450a, 450b, which releases the suction in the injection chamber 408, and the release of the first spring 457, which urges the needle 416 back through the seal 465 into the channel 407.

Figure 5A:
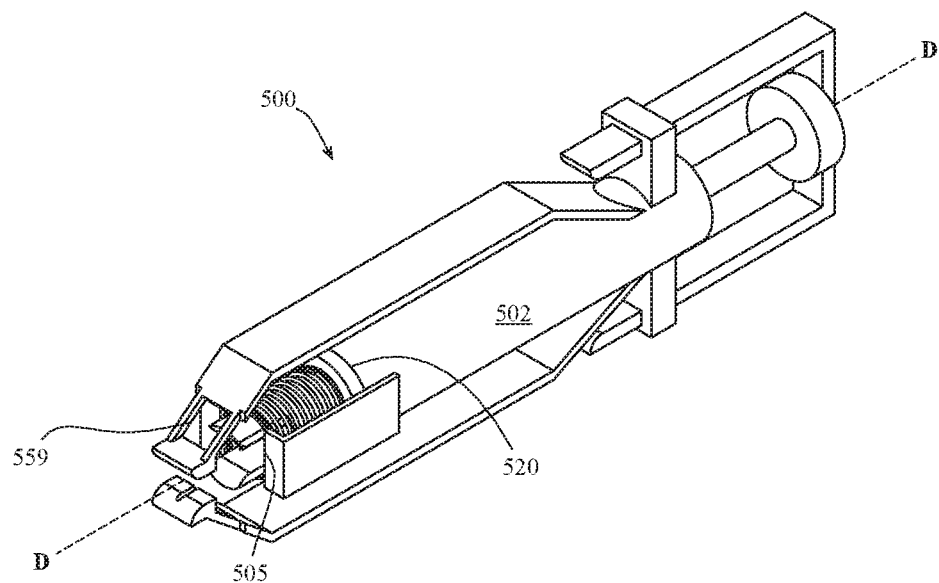
FIGS. 5A-5C illustrate an injection device according to another implementation.
Figure 5B:
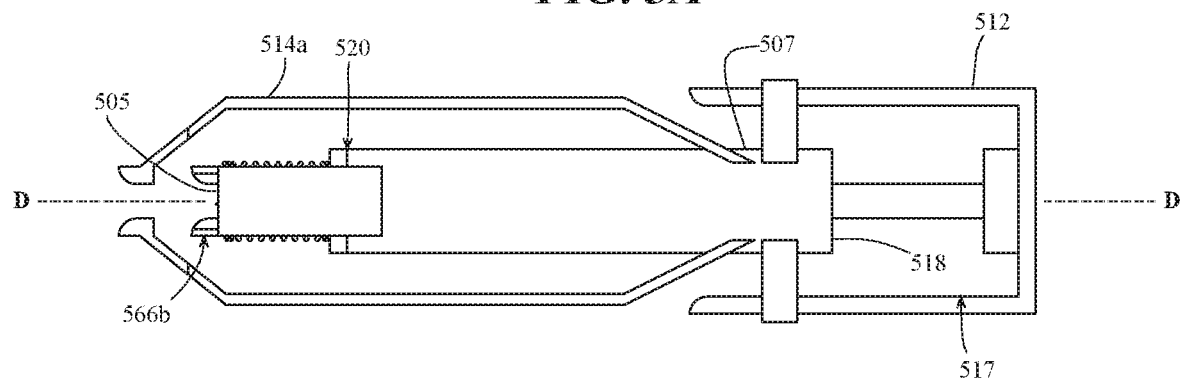
Figure 5C:
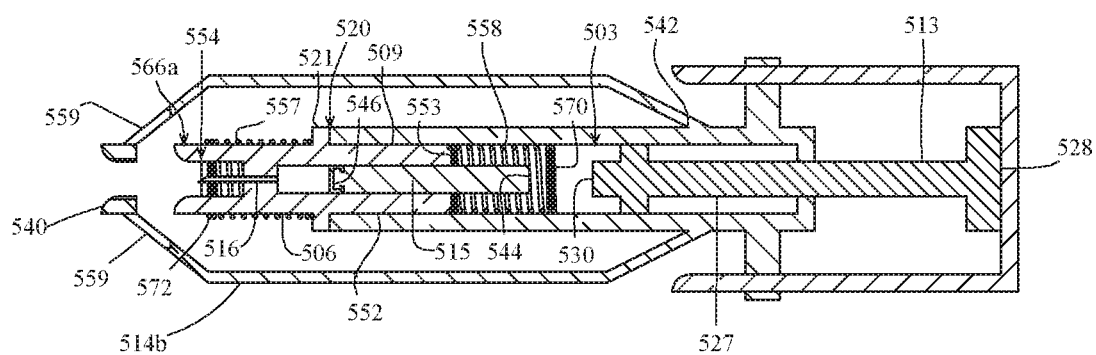

FIGS. 5A-5C illustrate a grasper-based tissue lifting device 500 according to another implementation. The device 500 includes a housing 502, an actuator 512, at least two grasping arms 514a, 514b, an injectable composition housing 506, needle 516, first spring 557, and second spring 558.

The housing 502 has a proximal end 518, a distal end 520, and a central longitudinal axis D-D extending there between. The housing 502 defines a channel 503 along at least a portion of the central longitudinal axis D-D adjacent the proximal end 518. At least a portion of the injectable composition housing 506 is disposed within the channel 503 adjacent the distal end 520 of the housing 502.

The actuator 512 includes a central arm 513 extending along the axis D-D and at least one peripheral surface 517. The at least one peripheral surface 517 is radially spaced apart from the central arm 513 and an exterior surface 507 of the housing 502. The central arm 513 has a proximal end 528 and a distal end 530. The distal end 530 of the central arm 513 of the actuator 512 is disposed within the channel 503, and the proximal end 528 extends away from the housing 502. A distal portion 527 of the central 513 arm, which is adjacent the distal end 530 of the arm 513, is slidably disposed within the channel 503 of the housing 502.

Each of the grasping arms 514a, 514b has a free end 540 disposed adjacent the distal end 520 of the housing 502 and a fixed end 542 coupled to the housing 502 proximally from the distal end 520 of the housing 502. Each arm 514a, 514b is bendable about its fixed end 542.

The injection plunger 515 is disposed along the central longitudinal axis D-D of the housing 502 and distally of the actuator 512. The injection plunger 515 has a proximal end 544 disposed axially adjacent the distal end 530 of the central arm 513 of the actuator 512 and a distal end 546.

The injectable composition housing 506 includes a proximal portion 552 that is disposed within the channel 503 of the housing 502 and a distal portion 554 that extends outside of the housing 502. A flange 521 extends radially outwardly from an external surface 509 of the injectable composition housing 506 between the proximal portion 552 and the distal portion 554. The distal portion 554 includes two arms 566a, 566b that extend axially distally and are spaced apart from each other relative to central axis D-D. The needle 516 is coupled to the injectable composition housing 506 and is disposed between the arms 566a, 566b. The injectable composition housing 506 is slidable within the channel 503. The needle 516 is in fluid communication with the injectable composition stored within the injectable composition housing 506.

The first spring 557 is disposed between distal flanges 505 coupled to and extending distally from the distal end 520 housing 502 and the flange 521. The second spring 558 is disposed around the injection plunger 515 and abuts the proximal end 553 of the proximal portion 552 of the injectable composition housing 506. The stiffness of the second spring 558 is greater than the stiffness of the first spring 557.

In operation, axial force on the actuator 512 in the distal direction causes the peripheral surface 517 to slide over the arms 514a, 514b, which bends the arms 514a, 514b about the fixed ends 542 of the arms 514a, 514b and translates the free ends 540 of the arms 514a, 514b laterally toward each other. This lateral movement of the free ends 540 allows the free ends 540 to grasp tissue adjacent the free ends 540. Further axial movement of the actuator 512 in the distal direction causes the distal end 530 of the central arm 513 to engage a proximal end 570 of the second spring 558, and the second spring 558 translates the axial movement of the actuator 512 to the injectable composition housing 506, urging the injectable composition housing 506 distally. Axial movement of the injectable composition housing 506 urges the distal end 572 of the first spring 557 into contact with the distal flange 505, which compresses the first spring 557 between the distal flange 505 and flange 521. In addition, axial movement of the injectable composition housing 506 causes the needle 516 to move distally relative to the distal flanges 505 of the housing 502, allowing the needle 516 to penetrate the tissue grasped by the free ends 540. The free ends 540 define openings 559 through which the distal ends of arms 566, 566b extend, which prevents the free ends 540 from translating away from each other while the injectable composition is being delivered through the needle 516.

The distal end 546 of the injection plunger 515 is disposed adjacent the proximal portion 552 of the injectable composition housing 506 prior to delivery of the injectable composition. Further axial movement of the distal end 530 of the central arm 513 toward the distal end 520 of the housing 502 urges the distal end 530 of the central arm 513 to compress the second spring 558 and engage the proximal end 544 of the injection plunger 515, causing axial movement of the distal end 546 of the injection plunger 515 through the injectable composition housing 506 to urge the injectable composition through the needle 516.

Figure 6:
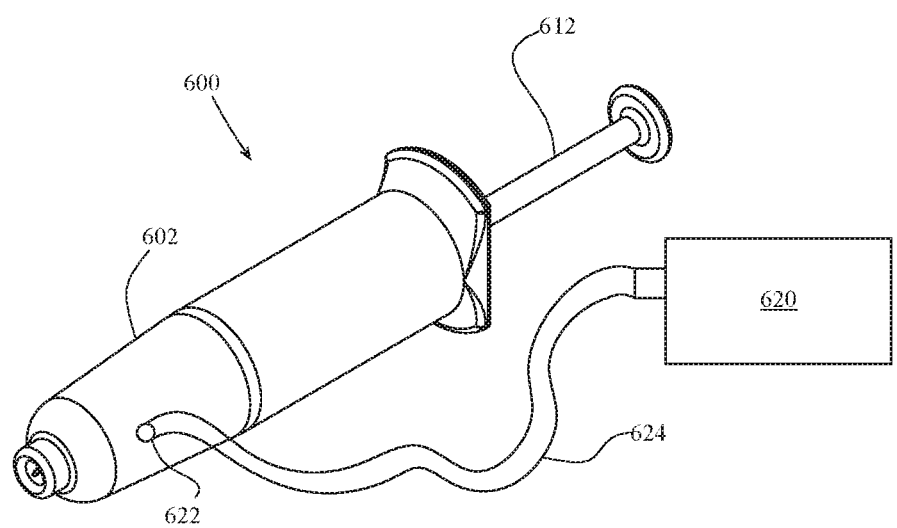
FIG. 6 illustrates an injection device according to another implementation.

In the implementations described above, the devices include an aspiration plunger and an injection plunger. However, in other implementations, the device includes one or more plungers. In the implementations described above in relation to FIGS. 1A-4B, suction forces are provided by increasing the volume of a sealed volume in fluid communication with a tissue by moving a plunger axially relative to a housing. However, in other implementations, such as is shown in FIG. 6, the suction force is provided by a vacuum source 620 that is separate from the one-handed operable device 600. The vacuum source 620 is in fluid communication with the device 600. For example, as shown in FIG. 6, the vacuum source 620 is coupled to the device 600 via a port 622 defining in the housing 602.

In the implementations described above, the plungers are axially movable along the central axis of the housing in which the plungers are disposed. However, in other implementations, one or more plungers are radially offset from the central axis.

Various modifications of the devices and methods in addition to those shown and described herein are intended to fall within the scope of the appended claims. Further, while only certain representative devices and method steps disclosed herein are specifically described, other combinations of the devices and method steps are intended to fall within the scope of the appended claims, even if not specifically recited. Thus, a combination of steps, elements, components, or constituents may be explicitly mentioned herein; however, other combinations of steps, elements, components, and constituents are included, even though not explicitly stated. The term "comprising" and variations thereof as used herein is used synonymously with the term "including" and variations thereof and are open, non-limiting terms. Those skilled in the art who review this disclosure will readily appreciate that many modifications are possible (e.g., variations in sizes, dimensions, structures, shapes and proportions of the various elements, values of parameters, mounting or layering arrangements, use of materials, colors, orientations, etc.) without materially departing from the novel teachings and advantages of the subject matter described herein. For example, elements shown as integrally formed may be constructed of multiple parts or elements, the position of elements may be reversed or otherwise varied, and the nature or number of discrete elements or positions may be altered or varied. Other substitutions, modifications, changes and omissions may also be made in the design, operating conditions and arrangement of the various example embodiments without departing from the scope of the present embodiments.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

The invention claimed is:

1. A suction-based injection device comprising:
  a housing having a proximal end, a distal end, and a central axis extending between the proximal end and the distal end, the housing defining:
    an aspiration chamber adjacent the proximal end of the housing;
    an injection chamber adjacent the distal end of the housing;
    an injectable composition chamber disposed between the aspiration chamber and the injection chamber along the central axis; and
    at least one connecting channel having a first opening in fluid communication with the injection chamber and a second opening in fluid communication with a proximal portion of the aspiration chamber;
  a plunger having a proximal end and a distal end, the distal end of the plunger being slidably disposed within the aspiration chamber, and the proximal end of the plunger extending axially from the proximal end of the housing; and
  a needle disposed within the injection chamber, the needle having a distal end disposed adjacent a distal end of the injection chamber,
  wherein:
    the proximal portion of the aspiration chamber is defined between a first seal and a second seal, the first seal extending radially between the plunger and the aspiration chamber at a first axial location along the plunger and the second seal being disposed adjacent the distal end of the aspiration plunger at a second axial location along the plunger, wherein the first axial location is disposed between the second axial location and the proximal end of the housing, the first seal is stationary, the second seal is axially moveable with the plunger, and an outer diameter of the second seal abuts an inner diameter of the aspiration chamber, a sealed volume is defined by the injection chamber, a surface against which a distal end of the injection chamber is disposed, the connecting channel, and the proximal portion of the aspiration chamber, and movement of the second seal of the plunger in a distal direction reduces a pressure in the injection chamber.

2. The suction-based injection device of claim 1, wherein the plunger is an aspiration plunger, and the device further comprises an injection plunger, the injection plunger comprising a proximal end and a distal end, wherein the proximal end of the injection plunger is disposed distally of the second seal of the aspiration plunger along the central axis.

3. The suction-based injection device of claim 2, wherein a third seal is disposed adjacent the distal end of the injection plunger, the third seal having an outer diameter that abuts an inner diameter of the injection chamber.

4. The suction-based injection device of claim 3, wherein a compression spring is disposed between the proximal end of the injection plunger and the distal end of the aspiration plunger, and a minimal force required to compress the compression spring is greater than a force required to move the injection plunger distally through the injectable composition chamber.

5. The suction-based injection device of claim 4, wherein the housing further defines at least one aspiration reset channel having a first opening defined by a radial wall of the aspiration chamber and a second opening defined by an exterior surface of the housing, the first opening being in communication with the sealed volume upon the distal end of the aspiration plunger compressing the spring.

6. The suction-based injection device of claim 2, wherein a compression spring is disposed between the proximal end of the injection plunger and the distal end of the aspiration plunger, and a minimal force required to compress the compression spring is greater than a force required to move the injection plunger distally through the injectable composition chamber.

7. The suction-based injection device of claim 1, wherein an injectable composition is disposed within the injectable composition chamber.

8. The suction-based injection device of claim 7, wherein the injectable composition comprises a therapeutic or diagnostic agent.

9. The suction-based injection device of claim 1, wherein the injectable composition is disposed within a cartridge, and the cartridge is disposed within the injectable composition chamber.

10. The suction-based injection device of claim 1, wherein the distal end of the injection chamber has an elliptical cross sectional shape as taken through a plane that is orthogonal to the central axis.

11. The suction-based injection device of claim 10, wherein the distal end of the injection chamber has an arcuate cross sectional shape as taken through a plane that includes the central axis.

12. The suction-based injection device of claim 1, wherein the distal end of the injection chamber has a circular cross sectional shape as taken through a plane that is orthogonal to the central axis.

13. The suction-based injection device of claim 12, wherein the distal end of the injection chamber has an arcuate cross sectional shape as taken through a plane that includes the central axis.

14. The suction-based injection device of claim 1, wherein the distal end of the injection chamber is coated with at least one bioadhesive agent.

15. The suction-based injection device of claim 14, wherein the bioadhesive agent is a mucoadhesive polymer.

16. The suction-based injection device of claim 1, wherein an exterior surface of the housing adjacent the proximal end of the housing defines at least one flange that extends radially outwardly from the proximal end.

17. The suction-based injection device of claim 1, wherein the needle is stationary within the device.

18. The suction-based injection device of claim 1, wherein the at least one connecting channel comprises a first connecting chamber and a second connecting channel.

* * * * *